United States Patent
Koertge

(10) Patent No.: US 7,379,533 B2
(45) Date of Patent: May 27, 2008

(54) COLLISION RESOLUTION IN X-RAY IMAGING SYSTEMS

(75) Inventor: Detlef Koertge, Carpentersville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 91 days.

(21) Appl. No.: 11/484,207

(22) Filed: Jul. 11, 2006

(65) Prior Publication Data

US 2007/0211861 A1 Sep. 13, 2007

Related U.S. Application Data

(60) Provisional application No. 60/781,151, filed on Mar. 10, 2006.

(51) Int. Cl.
*H05G 1/26* (2006.01)
(52) U.S. Cl. ...................................... 378/117; 378/197
(58) Field of Classification Search ................ 378/117, 378/205, 20, 208, 209, 65, 196, 197
See application file for complete search history.

(56) References Cited

U.S. PATENT DOCUMENTS

| | | | |
|---|---|---|---|
| 5,097,495 A * | 3/1992 | Gray et al. ................ 378/117 |
| 5,485,502 A | 1/1996 | Hinton et al. |
| 5,878,112 A * | 3/1999 | Koertge ...................... 378/209 |
| 6,560,307 B2 * | 5/2003 | Marume ........................ 378/4 |
| 6,651,279 B1 | 11/2003 | Muthuvelan |
| 6,941,199 B1 * | 9/2005 | Bottomley et al. ........... 701/23 |
| 7,046,765 B2 | 5/2006 | Wong et al. |
| 2003/0016786 A1 | 1/2003 | Horsbaschek |
| 2003/0176783 A1 | 9/2003 | Hu |
| 2004/0042587 A1 * | 3/2004 | Deshpande ................. 378/198 |
| 2005/0094770 A1 | 5/2005 | Fadler et al. |
| 2005/0114996 A1 | 6/2005 | Somasundaram |
| 2005/0226377 A1 * | 10/2005 | Wong et al. .................. 378/65 |
| 2005/0281374 A1 | 12/2005 | Cheng et al. |
| 2006/0133572 A1 | 6/2006 | Wong et al. |
| 2006/0133573 A1 | 6/2006 | Wong et al. |

FOREIGN PATENT DOCUMENTS

| JP | 11151236 A | 6/1999 |
|---|---|---|
| JP | 2001 104289 A1 | 4/2001 |

* cited by examiner

*Primary Examiner*—Hoon Song
(74) *Attorney, Agent, or Firm*—Peter Kendall

(57) ABSTRACT

A method and system for detecting a collision state between various elements of an x-ray imaging apparatus and/or a patient when they occur and resolving the collision state by reversing the movement of the x-ray imaging apparatus along the same path traveled which led to the collision state in the first instance.

18 Claims, 5 Drawing Sheets

| VECTOR | 0 | 1 | 2 | 3 | 4 | 5 | 6 |
|---|---|---|---|---|---|---|---|
| TIME | 11:15:41:18 | 11:15:41:20 | 11:15:41:22 | 11:15:41:24 | 11:15:41:26 | 11:15:41:28 | 11:15:41:30 |
| RAO/LAO | 0 | 0 | -1 | -4 | -7 | -7 | -7 |
| CRANI/CAUD | -5 | -5 | -5 | -10 | -15 | -15 | -15 |
| SID | 91 | 91 | 91 | 91 | 91 | 91 | 91 |
| TABLE-X | 20 | 20 | 20 | 20 | 20 | 21 | 21 |
| TABLE-Y | 13 | 13 | 13 | 13 | 13 | 13 | 13 |
| TABLE-Z | 2 | 2 | 2 | 1 | 2 | 2 | 1 |
| TABLE-TILT | 0 | 0 | 0 | 0 | 0 | 0 | 0 |

| VECTOR | 7 | 8 | 9 | 10 | 11 | 12 | 13 |
|---|---|---|---|---|---|---|---|
| TIME | 11:15:41:32 | 11:15:41:34 | | | | | |
| RAO/LAO | -3 | 0 | | | | | |
| CRANI/CAUD | -15 | -15 | | | | | |
| SID | 91 | 91 | | | | | |
| TABLE-X | 20 | 20 | | | | | |
| TABLE-Y | 13 | 13 | | | | | |
| TABLE-Z | 2 | 2 | | | | | |
| TABLE-TILT | 0 | 0 | | | | | |

FIG. 5

COLLISION RESOLUTION IN X-RAY IMAGING SYSTEMS

PRIORITY CLAIM TO RELATED APPLICATION

This application claims priority from U.S. Provisional Application Ser. No. 60/781,151 filed on Mar. 10, 2006, the entire contents of which is incorporated herein by reference.

FIELD OF THE INVENTION

The invention relates to new and useful improvements in medical systems. More particularly, the invention relates to a collision resolution system and method for use in an x-ray imaging system.

BACKGROUND OF THE INVENTION

Presently, angiographic x-ray systems are equipped with an automated collision protection function to avoid collisions of the various hardware components of the system with each other and, more importantly, with the patient. However, in some cases where the collision situation is not obvious to a system operator, collision events can still occur since the operator is allowed to override the warning until a physical collision occurs. One type of collision event that occurs with a fairly high degree of regularity is collisions of the tube underneath the patient table. These collisions occur fairly frequently because this area is not visible to the operator.

To resolve a collision event in present day angiographic x-ray systems, an override function is required to be activated by the operator. This is a necessary precaution because all motorized movements are blocked when a physical collision is detected. In those cases where an override is activated, the system allows the operator to move the system components in a very slow mode to resolve the collision event. In many cases the collision event is not obvious (e.g. the tube underneath the patient table) and it takes a significant amount of time and experience to move the system out of the collision situation. This is particularly true where a given position may be apparently reached with more than one set of axes motions but where motion limits on one or more axes produces a "dead end" requiring a time consuming backtracking in order to reach the desired position. In some cases, the patient must be removed from the system to avoid injury to quickly resolve a potentially dangerous and harmful situation.

From the foregoing it will be understood that there is a need for providing a collision detection system and method to maintain operational safety while providing the system operator with means for quickly and easily resolving a collision state.

SUMMARY OF THE INVENTION

A collision detection and resolution system and method of the invention addresses the afore-mentioned and other deficiencies of the prior art by detecting a collision state between various elements of an x-ray imaging apparatus and/or a patient when they occur and resolving the collision state by reversing the movement of the x-ray imaging apparatus along the same path traveled which led to the collision state in the first instance.

A collision detection and resolution system, according to one embodiment, comprises a control computer having at least one processor for acquiring position data of the most recent movements of an x-ray imaging apparatus, a memory for storing the acquired position data and a user interface for transmitting control signals to the at least one processor for instructing the processor to resolve a collision state, when it occurs, by using the acquired position data to move the x-ray imaging apparatus, by means of motorized drives, in the reverse direction of the apparatuses' most recent movement.

One of several advantages of the collision detection and resolution system of the invention is that collision resolution is easily implemented by a system operator using a standard interface device, such as a joystick, to initiate and control the resolution process. Another advantage of the present invention is that it provides a straightforward solution for resolving collision situations by using existing system information (i.e., the stored trajectory of the most recent movement of the x-ray imaging apparatus) together with the pre-existing motorized drives of the x-ray imaging system.

BRIEF DESCRIPTION OF THE DRAWINGS

These and other objects, features and advantages of the present invention will now be apparent from a consideration of the following Detailed Description Of Exemplary Embodiments when considered in conjunction with the drawing Figures, in which:

FIG. 5 illustrates a block diagram of a ring buffer memory area.

DETAILED DESCRIPTION OF EXEMPLARY EMBODIMENTS

In the following description, various operating parameters and components are described for one constructed embodiment. These specific parameters and components are included as examples and are not meant to be limiting.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between the various modules (or the logic flow of method steps) may differ depending upon the manner in which the present invention is programmed. Given the teachings herein, one of ordinary skill in the related art will be able to contemplate these and similar implementations of the present invention.

Figure 1:
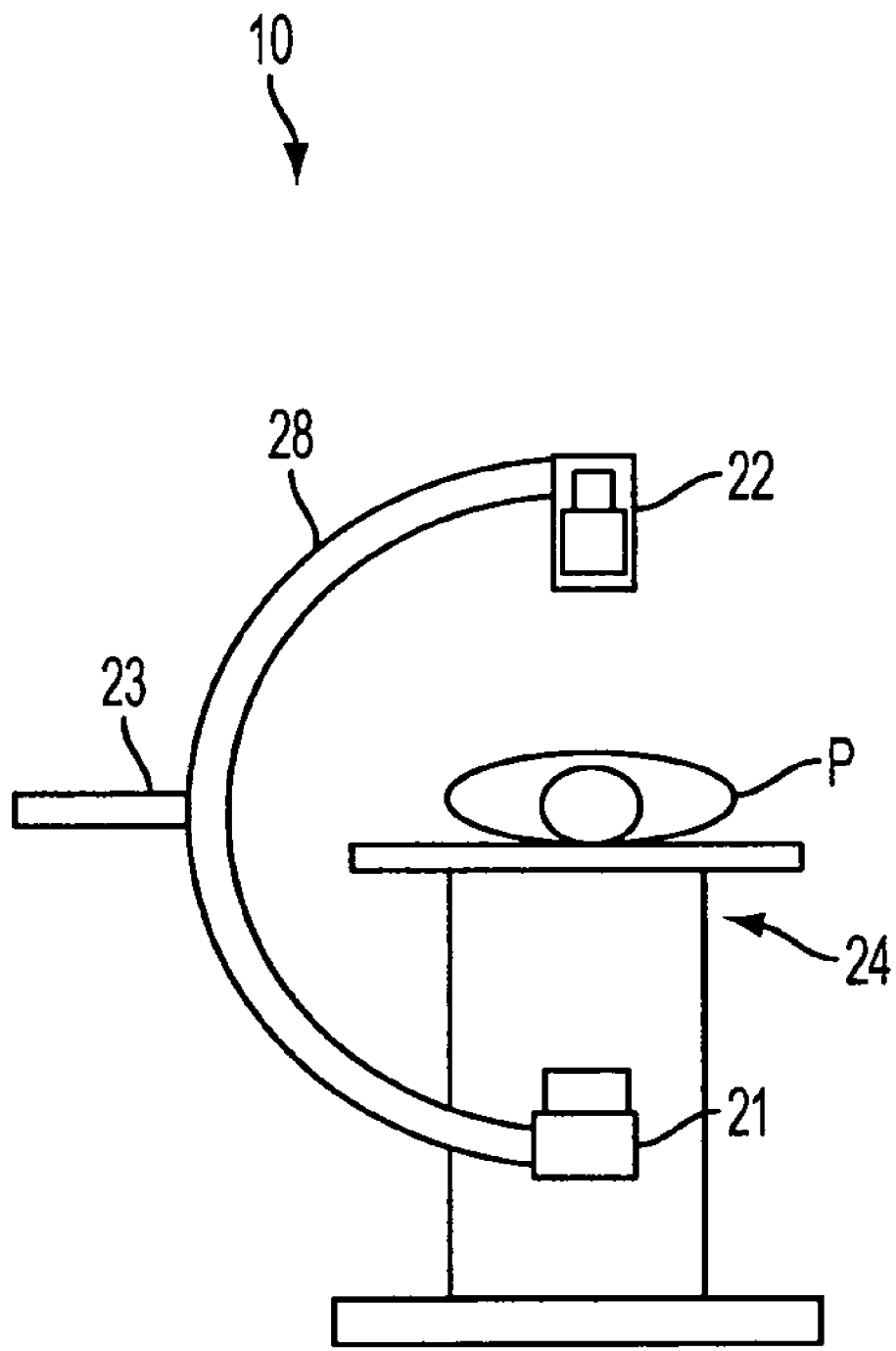
FIG. 1 is a perspective view of an x-ray imaging system according to an embodiment of the present invention.

Turning now to the drawings and, with particular attention to FIG. 1, an external view of a C-arm structure included in an X-ray diagnostic imaging system 10 is shown.

In the X-ray diagnostic imaging system 10, the X-ray tube 21 held by the C-arm structure is an under table X-ray tube type. Alternatively, the structure may be an over table X-ray tube type. There is also shown a patient (P) lying on a patient table 24.

As shown in FIG. 1, the X-ray tube 21 is disposed at one end of a C-arm 28, and the X-ray detecting unit 22 is disposed on the other end of the C-arm 28 such that the X-ray tube 21 and the X-ray detecting unit 22 oppose each other.

The C-arm 28 can slide such that the X-ray tube 21 moves from the lower position to the upper left position in the drawing, or such that the X-ray detecting unit 22 moves from the upper position to the lower left position in the drawing. Furthermore, the C-arm 28 can rotate around a rotational axis of the rotating mechanism 23.

The X-ray diagnostic imaging system 10 includes a computer (not shown) functioning as a controlling unit that drives various units to capture the contrast images.

Figure 2:
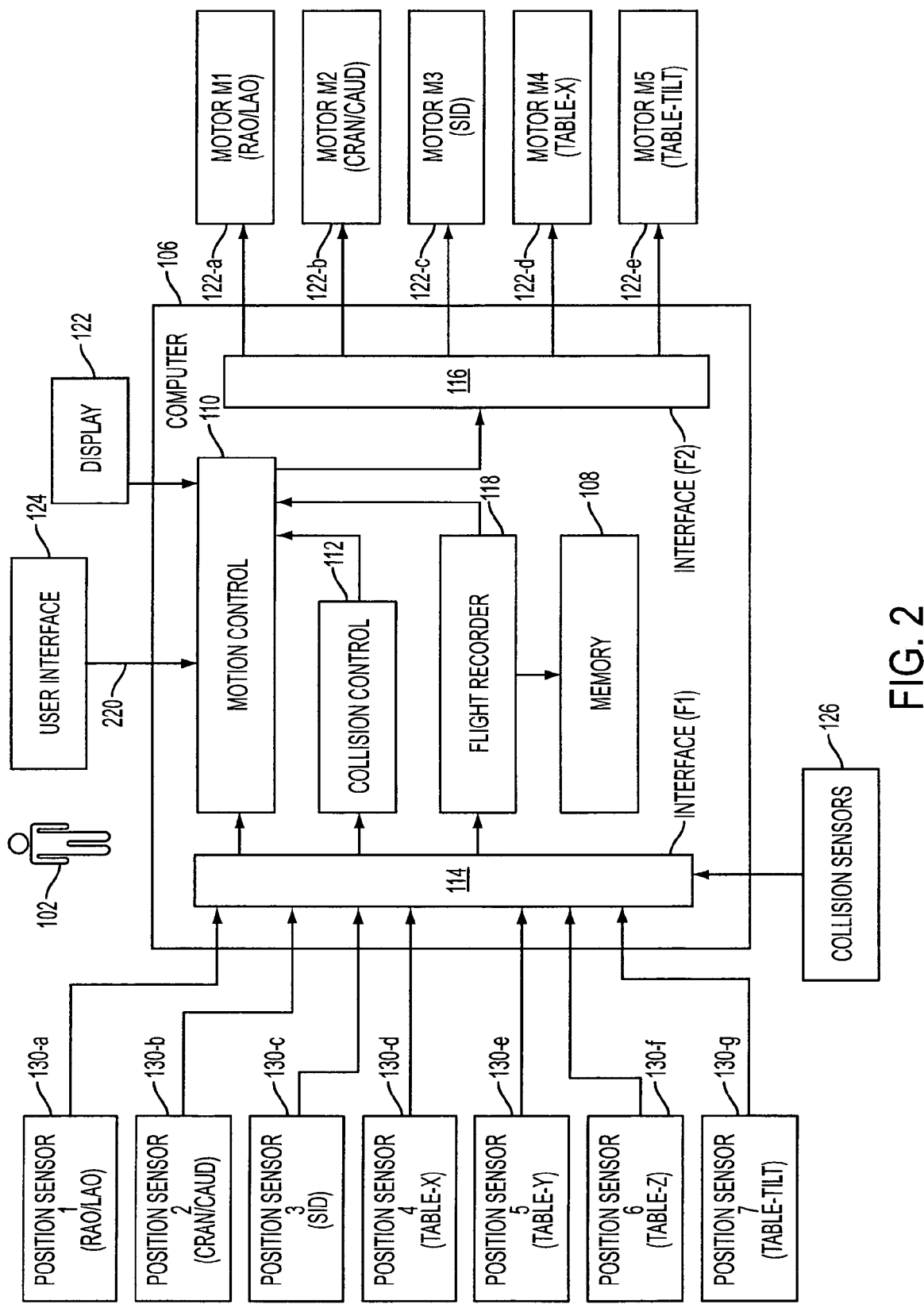
FIG. 2 is a more detailed diagram of novel and conventional elements of a prior art computer used to control the radiation treatment device of FIG. 1.

Referring now to FIG. 2, there is shown a block diagram showing the components of a computer system 106, which can be used to drive the various units of the x-ray system diagnostic imaging system 10 to capture the contrast images. The computer system 106 includes a system memory 108, a motion control module 110, a collision control module 112, first (F1) 114 and second (F2) 116 data interfaces, and a module 118 for performing collision resolution in accordance with embodiments of the invention, referred to hereafter as a "flight recorder" module 118. It is understood that each of the modules 110, 112 and 118 are capable of performing the standard functions of a computer including the ability to perform calculations and logic operations required to execute a program.

In the exemplary illustrative embodiment, an operator 102 interfaces with the x-ray diagnostic system 10 via a user interface 124, which comprises a joystick and a dead man's switch. The C-arm 28 is controlled externally by the operator 102 using the joystick. Manipulation of the joystick 124 by the operator 102 creates control data (signals) which are sent to the motion control module 110 via interface connector 220. The motion control module 110 uses the control data, received via interface connector 220, to control the various motors M1 122a, M2 122b, M3 122c, M4 122d and M5 122e of the x-ray diagnostic system 10, via the second (F2) data interface 116, to move the C-arm 28.

Each of the motors M1 122a, M2 122b and M3 122c control various angular rotations of the C-arm structure. For example: Motor M1 122-a controls the left/right angular rotation of the C-arm 28, (RAO/LAO (Right Anterior Oblique/Left Anterior Oblique). Motor M2 122-b controls the top and bottom angular rotations of the C-arm 28, (CRAN/CAUD (cranial/caudal)). Source image distance (SID) movement between the x-ray tube and the image receptor is controlled via motor M3 122-c.

Linear movement in the x-direction of the patient table 24 is effected via motor M4 122-d (Table-X) and tilting movement of a patient table 24 is effected via motor M5 122-e (Table-Tilt). In other embodiments, motors M4 and M5 may be substituted for mechanical linkage operated via manual means.

Feedback of the current position of the various axes of the C-arm 28, under motor control is received at the first data interface F1 114 from position sensors 130a through 130g configured to detect a current position of each axis. As various position sensor data is received at the computer 106, it is stored in the system memory 108.

In an exemplary embodiment, at least a portion of the system memory 108 is configured in a ring buffer configuration. As is well known in the art, in a ring buffer configuration, newly written data overwrites old, previously stored data.

The collision control unit 112 is configured to monitor the actual positions of the C-arm 28, the patient table 24 and the source-image distance (SID) when a collision state is entered.

Whenever the x-ray diagnostic system 10 enters a collision zone, the velocity of the axes currently in motion of the x-ray system are reduced. A collision zone is generally defined herein as a zone around an object at a given distance from the object. In other embodiments, a "collision state" may be used in lieu of a collision zone. A collision state may be defined as a state in which a device receptor actually touches another-surface, including the patient, upon which all motion is immediately suspended. In the presently described embodiment, a "collision state" may be detected by one or more system collision sensors 126. It is noted that the embodiments of the invention contemplate the use of both collision zones and collision states in various embodiments.

The flight recorder module 118 of the invention is configured to operate in one of two modes, normal and resolve.

The flight recorder module 118 determines which mode it is currently operating in (i.e., normal or resolve) based on a binary input signal received from the collision control module 112 which determines whether or not a collision zone has been entered or a collision state has occurred. For example, a binary input signal value of 0 could indicate that the system 10 is presently in a 'normal' mode and a binary input signal value of 1 could indicate that the system is in a 'resolve' mode.

In the normal mode of operation, the flight recorder module 118 formats and stores the most recent movements (e.g., the last 10 seconds) of the C-arm 28 and patient table 24 as a series of time-stamped vectors, received via interface F1 114 in the system memory 108.

In the resolve mode of operation, the flight recorder module 118 of the invention resolves a detected collision state of the x-ray imaging system 10 as follows.

When a collision state is detected by the collision control module 112, the time-stamped vectors which are currently stored in the system memory 108 are frozen in the memory. It is noted that the frozen values constitute the most recent movement of the system 10 prior to entering the resolve mode upon detecting a collision state.

When the operator initiates the process of collision resolution, typically in response to a system message on display 122, the data values, frozen in the system memory 108, are individually read out from the system memory 108 by the flight recorder module 118 in the reverse order in which they were written. In other words, the last vector to be written to the system memory 108 is the first vector to be read out from the system memory 108.

As the vector values are read out from the system memory 108 in reverse order, they control the various system motors M1-M5 to produce a reverse trajectory of the most recent movements of the C-arm 28 controlled by motors M1-M3 and patient table 24 controlled motors M4-M5 which led to the occurrence of entering the collision state in the first instance. It is noted that in those configurations wherein the patient table 24 is controlled via mechanical means, suitable instructions may be displayed to the operator 102 via display 122, indicating the necessary operations to be performed on the table 24 to resolve the collision state.

In this embodiment, the operator 102 both initiates the process of collision resolution and controls the speed of the process (i.e., the reverse trajectory movement of the C-arm 28) by manipulating a joystick. In other embodiments, the operator 102 merely initiates the process of collision resolution via a button press without controlling the speed of the reverse trajectory movement. In these embodiments, the speed of the reverse trajectory movement is automatic.

Figure 3:
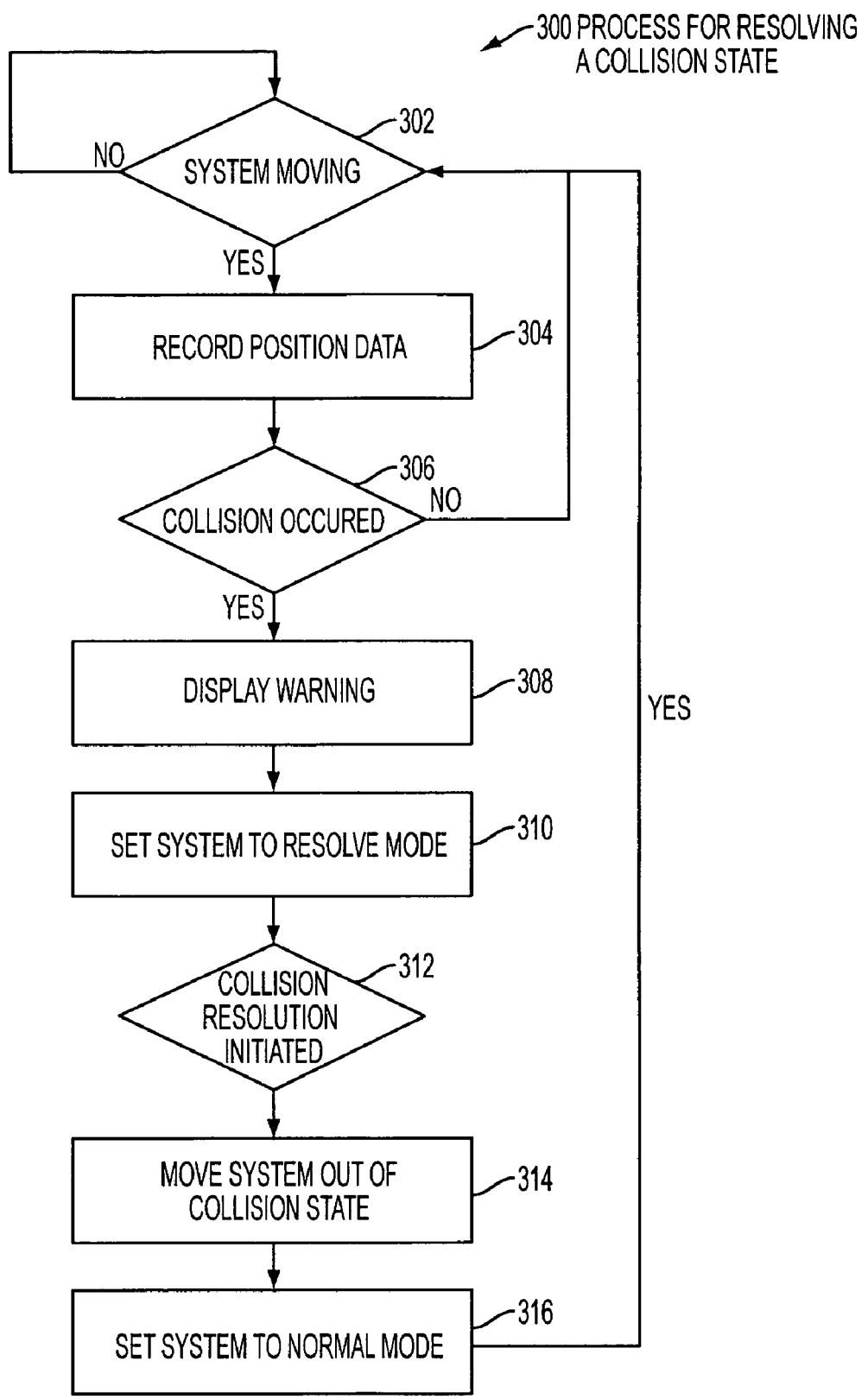
FIG. 3 is a flow chart illustrating a survey process in accordance with an embodiment of the present invention.

With reference now to FIG. 3 and certain elements of FIGS. 1 and 2, there is shown a process 300 for resolving a collision state in an x-ray imaging system 10 in accordance with the present invention.

At step 302, it is determined if the C-arm 28 is moving. Movement is determined by the motion control module 110 receiving changing position sensor inputs 130. If it is determined at this step that the C-arm 28 is moving, the process continues at step 304, otherwise the process remains at step 302 until movement is detected.

At step 304, position data associated with the movement of the C-arm 28 is recorded in the system memory 108. More particularly, position sensor data is continuously received by the inventive flight recorder module 118 from the various position sensors 130, via the first interface F1 114. The position sensor data is formatted by the inventive flight recorder module 118 and is stored in the system memory 108 in a format described further below.

At step 306, the collision control module 112 determines whether a collision has occurred. If it is determined that a collision has occurred, the process continues at step 308, otherwise, the process returns to step 302. Collision detection is determined by the collision control unit 112 by processing inputs received from the various position sensors 130 together with an internal software model of the physical x-ray system 10.

At step 308, a warning is displayed to the operator indicating that a collision zone is entered in an embodiment that employs collision zones or that a collision has occurred in an embodiment that employs collision states.

At step 310, the system 10 is automatically switched from normal mode to resolve mode in which all of the motor drives M1-M5 are stopped. To switch the system 10 from normal to resolve mode, the collision control module 112 sends a signal to the motion control module 110 to stop all motion. Thereafter, both the motion control module 110 and the flight recorder module 118 are set to 'resolve' mode.

At step 312, in the resolve mode, the system 10 waits for the operator 102 to initiate a collision resolution procedure. In the presently described embodiment, the collision resolution procedure is initiated by the operator holding down a dead man's switch while deflecting the joystick (i.e., user interface 124) a predetermined amount. In this embodiment, the velocity of the reverse motion of the C-arm 28 is controlled by the degree of deflection of the joystick applied by the operator 102. In other embodiments, the velocity of the reverse motion of the C-arm 28 may occur at a fixed rate. In these embodiments, the collision resolution procedure is initiated by a simple button press without further operator intervention.

At step 314, the collision resolution procedure, initiated at step 312, is performed, a more detailed explanation of which is provided in accordance with the detailed flowchart of FIG. 4, described below.

At step 316, upon completing the collision resolution procedure, the system 10 is reset to the normal mode and the process returns to step 302.

Figure 4:
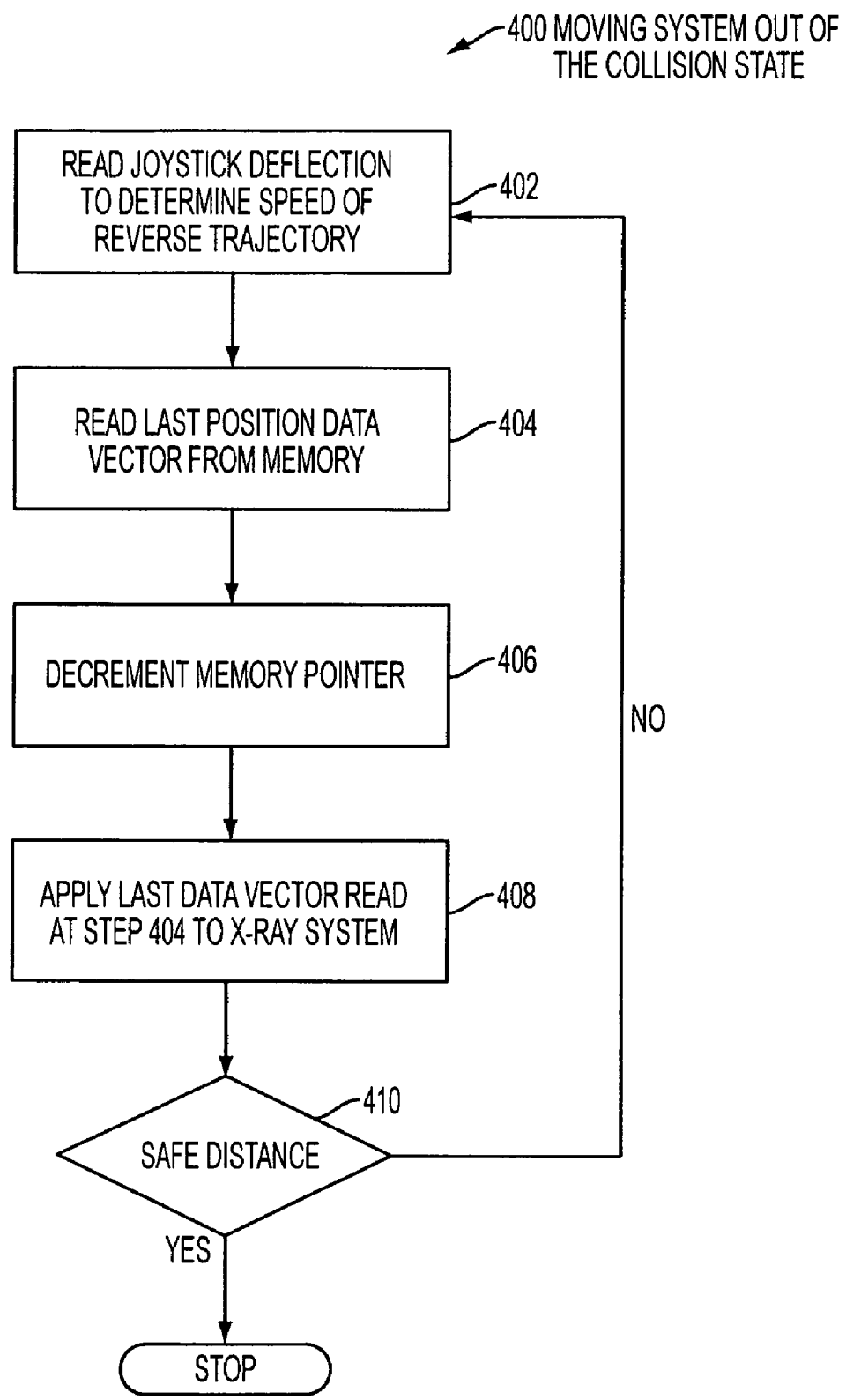
FIG. 4 is a more detailed flow chart of step 312 of the flowchart of FIG. 3, illustrating a process for performing collision resolution an embodiment of the present invention.

In FIG. 4 there is shown a more detailed process of step 312 of the flowchart of FIG. 3. Specifically, FIG. 4 is a detailed flowchart illustrating a process for performing collision resolution, in accordance with an embodiment of the present invention. With reference now to FIG. 4 and certain elements of FIGS. 1 and 2, the process begins at step 402.

At step 402, the motion control module 110 reads the degree of operator deflection of a user interface device (e.g., joystick deflection). The degree of deflection of the user interface device directly determines the speed (i.e., velocity) of the C-arm 28 moving along a reverse trajectory determined by the most recently stored data values in the system memory 108. More particularly, the deflection is used as a multiplier with an internal constant that controls the actual speed of the motors for moving from one position to another in accordance with the most recently stored data values in the system memory 108. As noted above, in other embodiments, the speed at which the C-arm 28 moves along a reverse trajectory may be set to a fixed value.

At step 404, the inventive flight recorder module 118 retrieves the last written stored movement (vector) of the C-arm 28 from the system memory 108, as indicated by a memory pointer.

At step 406, a memory pointer is decremented to point to the N-dimensional vector immediately preceding the N-dimensional time-stamped vector read at step 404.

At step 408, the N-dimensional time-stamped vector retrieved at step 404 is applied to the system 10 to cause the system 10 to move in a reverse trajectory in accordance with the N values.

At step 410, it is determined whether the C-arm 28 has been moved a so-called "safe distance" in a reverse direction. If so, the process for moving the C-arm 28 out of the collision state is complete. Otherwise, the process returns to step 402. It is noted that what determines a "safe distance" is configurable parameter which is set prior to system operation.

Referring now to FIG. 5, there is shown an exemplary illustrative embodiment of a ring buffer memory 500. The ring buffer memory 500 wraps stored data from the end of the memory (vector 17) area to the start of the memory area (vector 0). In the present embodiment, it is contemplated to utilize a portion of the system memory 108 for use as a ring buffer memory 500.

The ring buffer memory area 500 of FIG. 5 is shown to include 18 write positions (0-13) for ease of explanation. In various embodiments, the number of write positions may depend upon what constitutes the most recent movement of the C-arm 28.

Each write position of the ring buffer memory 500 (e.g., write positions 0-13 in the example) stores an N-dimensional time-stamped vector. For example, as shown in FIG. 5, vector 0 of the ring buffer memory, labeled 502, is an 8 dimensional vector including a time stamp value of 11:15:41:18 and seven vector values {0, −5, 91, 20, 13, 2, 0).

In accordance with the method of the invention for performing collision resolution, whenever motion occurs on any axis of the C-arm 28, that motion is detected by one or more of the system position sensors 130 and recorded as an N-dimensional time-stamped vector at a memory position pointed to by a memory pointer 50. For example, FIG. 5 illustrates the pointer 50 pointing to ring buffer position 8 (i.e., vector 8), corresponding to the most recently detected motion at time 11:15:41:34.

Whenever a collision state is detected, the data contents of the ring buffer memory area 500 are frozen and subsequently read in reverse order from the current pointer position, as determined by the memory pointer 50, to the first write position in the ring buffer memory 500 (i.e., vector 0), thus providing the flight recorder module 118 with the necessary data to move the C-arm 28 in a reverse trajectory of its most recent movement, as described at step 406 of the flowchart of FIG. 4.

There have thus been provided new and improved methods and systems for detecting and resolving a collision state in a x-ray imaging system. In the described embodiment of the invention, the invention comprises detecting a collision state between various elements of an x-ray imaging apparatus and/or a patient when they occur and resolving the collision state by reversing the movement of the x-ray imaging apparatus along the same path traveled which led to the collision state in the first instance. In accordance with benefits and advantages of the present invention, collision resolution is easily implemented by a system operator using a standard interface device, such as a joystick, to initiate and control the resolution process. Another advantage of the present invention is that it provides a straightforward solution for resolving collision situations by using existing system information (i.e., the stored trajectory of the most recent movement of the x-ray imaging apparatus) together with the pre-existing motorized drives of the x-ray imaging system.

While particular embodiments of the present invention have been illustrated and described, it would be obvious to those skilled in the art that various other changes and modifications can be made without departing from the spirit and scope of the invention. Any of the aspects of the invention of the present invention found to offer advantages over the state of the art may be used separately or in any suitable combination to achieve some or all of the benefits of the invention disclosed herein.

What is claimed is:

1. A collision detection and resolution system for resolving a collision state of an x-ray system, the system comprising:
    (a) a user interface configured to receive control signals from an operator for activating a collision state resolution process, and receive further control signals for controlling the movement of the x-ray system in a normal mode of operation;
    (b) a first system module configured to control the movement of the x-ray system in the normal mode of operation in accordance with position sensor input data received via the user interface, and determine the movement of the x-ray system in the normal mode of operation in accordance with changing position sensor input data;
    (c) a second system module configured to detect a collision state of the x-ray system, stop movement of the x-ray system in response to the detected collision state, and monitor at least one of a current position of the x-ray system, a patient table and a source-image distance (SID) of the x-ray system when the collision state is detected;
    (d) a third system module configured to format and store data values corresponding to the most recent movements of the x-ray system in the normal mode of operation, and resolve a detected collision state of the x-ray system in the resolve mode of operation by reading out the stored data values in the resolve mode of operation for use in controlling a reverse trajectory of the most recent movements of the x-ray system; and
    (e) storage means for storing the data values corresponding to the most recent movements of the X-ray system in the normal mode of operation.

2. The collision detection and resolution system according to claim 1, wherein the user interface is further configured to control the speed of movement of the x-ray system in the resolve mode of operation.

3. The collision detection and resolution system according to claim 1, further comprising a display device configured to display a warning upon detection of the collision state.

4. The collision detection and resolution system according to claim 1, wherein the third system module is further configured to format and store the most recent movements of the patient table.

5. The collision detection and resolution system according to claim 1, wherein the third system module determines an operational mode as one of normal or resolve based on an input signal received from the second system module.

6. The collision detection and resolution system according to claim 1, wherein the storage means comprises a ring buffer.

7. A method for resolving a collision state of an x-ray system, comprising:
    (a) determining if the x-ray system is moving;
    (b) recording position data corresponding to the most recent movement of the x-ray system;
    (c) determining if a collision state has occurred; and
    (d) resolving the collision state using the recorded position data to move the x-ray system by means of motorized drives in the reverse direction of the system's most recent movement.

8. The method according to claim 7, wherein said determination step (a) is made in accordance with changing position sensor input data generated by a moving x-ray system.

9. The method according to claim 7, wherein said step (b) of recording position data corresponding to the most recent movement of the x-ray system, further comprises:
    receiving position sensor data from a plurality of position sensors coupled to the x-ray system;
    formatting the received position sensor data; and
    storing the most recent formatted position sensor data in a system memory.

10. The method according to claim 9, wherein the system memory is configured as a ring buffer memory.

11. The method according to claim 10, wherein the position sensor data is stored in the ring buffer memory as a plurality of N-dimensional time-stamped vectors.

12. The method according to claim 11, wherein each of the plurality of N-dimensional time-stamped vectors comprise:
    a time stamp value;
    a first vector value corresponding to a left/right angular rotation of a C-arm assembly;
    a second vector value corresponding to a top/bottom angular rotation value of the C-arm assembly; and
    a third vector value corresponding to a source image distance of the C-arm assembly.

13. The method according to claim 7, wherein said step (c) of determining if a collision state has occurred further comprises:
    processing position sensor data received from a plurality of position sensors; and
    evaluating the processed position sensor data in accordance with an internal software model of the x-ray system.

14. The method according to claim 11, wherein said step (d) of resolving the collision state further comprises:
  displaying a warning to an operator upon detection of the collision state;
  terminating all drive motors of the x-ray system; and
  freezing the most recent formatted position sensor data in the memory, sequentially reading the most recent formatted position sensor data from the memory; and
  moving the x-ray system in a reverse direction in accordance with the most recent formatted position sensor data read from the memory.

15. The method according to claim 14, wherein the collision resolution procedure is manually initiated by an operator via a system user interface.

16. The method according to claim 14, further comprising:
  determining that a safe distance is achieved; and
  terminating the resolution of the collision state upon satisfying said determination.

17. The method according to claim 14, wherein the movement of the x-ray system in a reverse direction is a pre-determined fixed rate of movement.

18. The method according to claim 14, wherein the movement of the x-ray system in a reverse direction is manually controlled by an operator.

* * * * *